United States Patent [19]

Pichler

[11] Patent Number: 5,151,083
[45] Date of Patent: Sep. 29, 1992

[54] APPARATUS FOR ELIMINATING AIR BUBBLES IN AN ULTRASONIC SURGICAL DEVICE

[75] Inventor: Robert H. Pichler, Skokie, Ill.

[73] Assignee: Fibra-Sonics, Inc., Chicago, Ill.

[21] Appl. No.: 737,425

[22] Filed: Jul. 29, 1991

[51] Int. Cl.⁵ .................. A61B 17/00; A61M 1/00
[52] U.S. Cl. .................. 604/22; 128/24 AA;
606/107; 606/169; 604/19; 604/902
[58] Field of Search .............. 606/107, 166, 169, 170, 606/171; 604/19, 22, 48, 54; 128/35, 43, 305, 24 A, 749-754

[56] References Cited

U.S. PATENT DOCUMENTS

| | | | |
|---|---|---|---|
| 3,526,219 | 9/1970 | Balamuth | 128/24 AA |
| 3,805,787 | 4/1974 | Banko | 606/169 |
| 4,156,187 | 5/1979 | Murry et al. . | |
| 4,320,761 | 3/1982 | Haddad | 128/305 |
| 4,681,561 | 7/1987 | Hood et al. | 604/22 |
| 4,741,731 | 5/1988 | Starck et al. . | |
| 4,816,018 | 3/1989 | Parisi | 128/24 AA |
| 5,038,756 | 8/1991 | Kepley | 128/24 AA |

Primary Examiner—Stephen C. Pellegrino
Assistant Examiner—Glenn K. Dawson
Attorney, Agent, or Firm—Hill, Van Santen, Steadman & Simpson

[57] ABSTRACT

In an ultrasonic handpiece with irrigation an aspiration passages, an opening is made between the aspirating passage and the irrigating passage so as to remove bubbles from the operating site so that the surgeon's vision will not be obstructed.

2 Claims, 1 Drawing Sheet

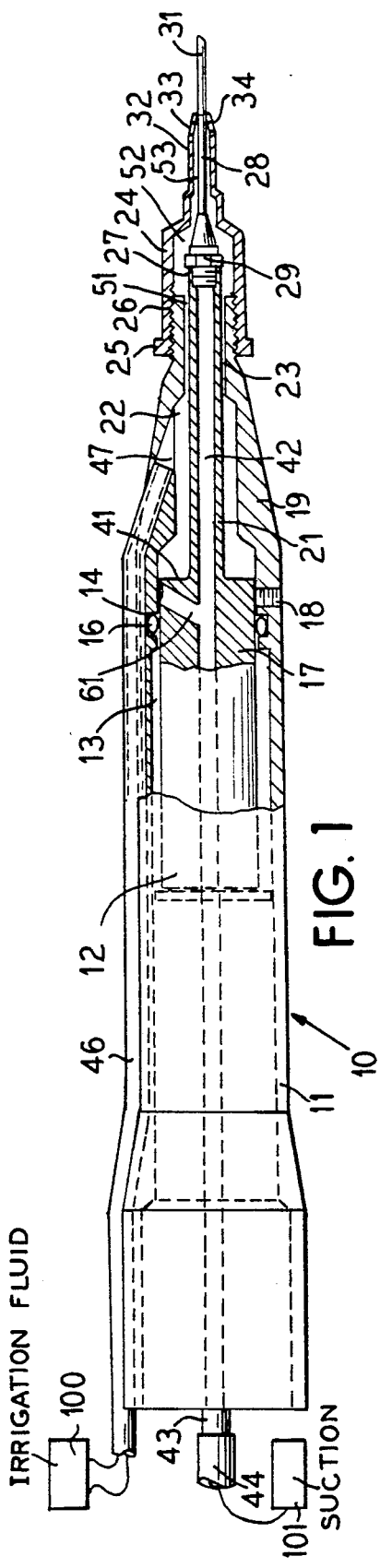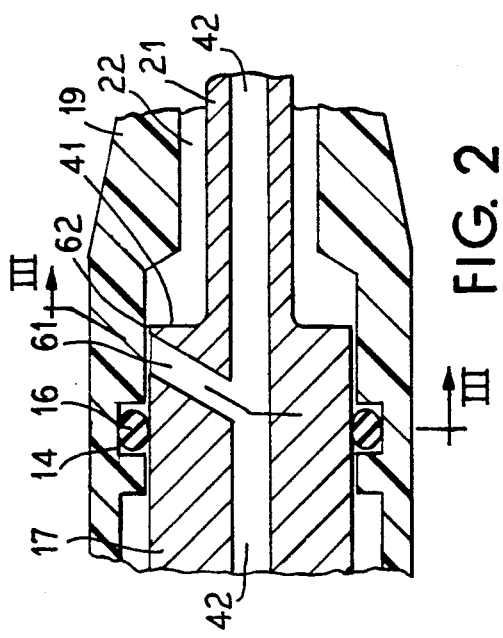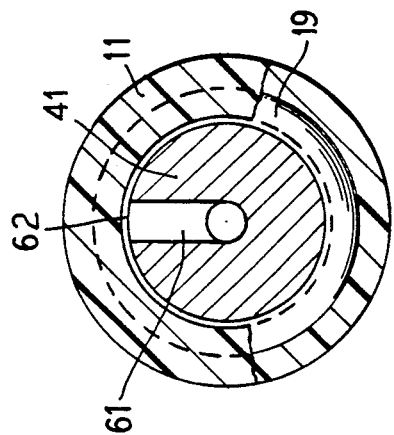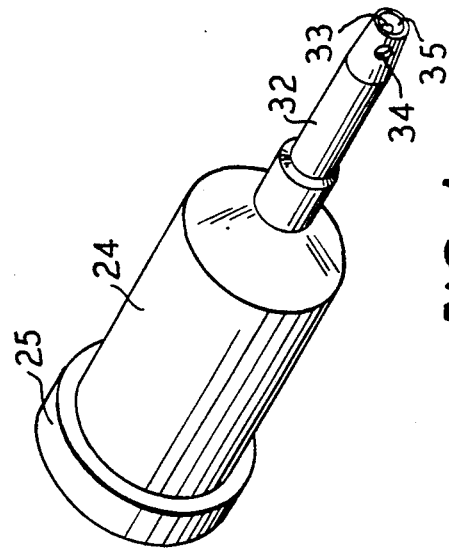

APPARATUS FOR ELIMINATING AIR BUBBLES IN AN ULTRASONIC SURGICAL DEVICE

CROSS-REFERENCES TO RELATED APPLICATIONS

Application entitled "Ultrasonic Needle With Sleeve Including A Baffle" in which the inventor is Sokhuom Khek identified in the attorney's record as Case No. P91,1410.

BACKGROUND OF THE INVENTION

1. Field of the Invention

This invention relates in general to ultrasonic handpieces for surgical use in particular to an improved ultrasonic handpiece.

2. Description of Related Art

U.S. Pat. Nos. such as 4,156,187 and 4,741,731 assigned to the assignee of the present application disclose ultrasonic transducers for surgical handpieces. Such devices provide irrigation and aspiration at the operating site. At times when irrigating fluid passes through the ultrasonic transducer handpiece, air can be mixed with the irrigation fluid so that bubbles occur at the operating site which reduces the visibility of the surgeon. Such bubbles are caused by the ultrasonic vibration of the driving transducer which causes air bubbles to be mixed with the irrigating fluid which is supplied to the operating site.

SUMMARY OF THE INVENTION

The present invention provides an air vent which passes between the aspirating tube and a chamber which communicates with the irrigation fluid supply so as to remove air and prevent the formation of air bubbles in the irrigation supply as it passes through the handpiece.

It is an object of the present invention to eliminate air bubbles in irrigation fluid supplied through an ultrasonic surgical handpiece by providing a suction opening between the aspiration tube and a chamber into which the irrigation fluid is supplied.

It is another object of the present invention to provide an improved ultrasonic surgical handpiece which eliminates the formation of bubbles during operations.

Other objects, features and advantages of the invention will be readily apparent from the following description of certain preferred embodiments thereof taken in conjunction with the accompanying drawings although variations and modifications may be effected without departing from the spirit and scope of the novel concepts of the disclosure, and in which:

DESCRIPTION OF THE DRAWINGS

FIG. 1 is a partially sectional view through the ultrasonic surgical handpiece of the invention;

FIG. 2 is an enlarged sectional view which shows the passage between the aspiration tube and the chamber to which the irrigation fluid is supplied;

FIG. 3 is a sectional view taken on line III—III from FIG. 2; and

FIG. 4 illustrates the sleeve which surrounds the operating needle.

DESCRIPTION OF THE PREFERRED EMBODIMENTS

FIG. 1 illustrates ultrasonic surgical handpiece 10 which has an outer cylindrical cover member 11 and an ultrasonic motor 12 is mounted in the cylindrical member 11. An opening 13 is formed between the ultrasonic motor 12 and the outer cylindrical portion 11 and a groove 14 is formed in the inner surface of the outer cylindrical member 11 in which an O-ring 16 is mounted between the member 11 and the ultrasonic motor 12 so as to provide a fluid seal. A set pin 18 is threadedly received in a threaded opening formed in the outer cylindrical member 11 and engages the motor member 12 to lock it as shown in FIG. 1.

A cylindrical extending portion 21 extends from the motor member 12 and has an internally threaded end 27 in which a threaded portion 29 of a needle 28 is threadedly received. The end 31 of the needle 28 comprises the operating needle which is used by the surgeon to cut tissue. A shoulder 41 is formed on the motor member 12 where the extension 21 joins the motor member. The outer cylindrical member 11 has a conical shaped extending portion 19 which extends around the portion 21 and is formed with an end 23 which has an externally threaded portion 26. A plastic collar 24 has an internally threaded portion 25 which is received on the threaded portion 26 and the sleeve 24 has a portion 32 which extends along the needle 28 and terminates before the end of the needle 21. Two irrigating openings 33 and 34 are formed in the sleeve 24 through which irrigation fluid is supplied.

An irrigation tube 46 receives irrigation fluid from a reservoir 100 and is connected to the cylindrical portion 11 of the handpiece and terminates in an opening 47 which supplies irrigation into a cavity 22 between the portion 19 and the portion 21. The irrigation fluid passes from the opening 22 through the opening 51 into the sleeve 24 and through portion 32 and cavity 53 and out openings 33 and 34. The needle 31 is hollow and communicates with an aspiration tube 42 which extends through the handpiece 10 and has an end 43 connected to an aspiration tube 44 that is connected to a suction pump 101 so that material can be removed from the operating site.

As best shown in FIGS. 1, 2 and 3, a hole 61 is formed between the aspirating tube 42 through the member 17 so that the aspirating tube 42 communicates with the cavity 22 through the space 62 between the end of opening 61 and the cavity 22 as shown in FIG. 2. With the handpiece in the horizontal position as shown in FIGS. 1, 2 and 3 the opening 61 might be formed at an angle of 30° from the vertical. The shoulder 41 on the motor 12 tends to form bubbles.

In operation, as irrigation fluid is supplied by the surgeon through the irrigating tube 46 into the cavity 22 and suction is supplied to tube 44 and tube 42 and the needle 31, suction will exist through the opening 61 and the spaces 62 and 22 which will remove bubbles from the irrigation fluid which is supplied to the cavity 22 so that such bubbles will not pass through the opening 51, cavities 52 and 53 and out the openings 33 and 34. Thus, the suction from tube 61 eliminates bubbles which occur in the prior art devices so that the surgeon's vision is not obstructed by such bubbles.

Irrigation fluid from the irrigation fluid supply 100 is supplied to tube 46 as shown in FIG. 1 and suction is supplied by the suction pump 101 to the aspirating tube 44.

Although the invention has been described with respect to preferred embodiments, it is not to be so limited as changes and modifications can be made which are within the full intended scope of the invention as defined by the appended claims.

I claim as my invention:

1. An ultrasonic handpiece comprising, an ultrasonic motor with an aspirating passage therethrough mounted in said handpiece and formed with a tubular shaped extending portion, suction means connected to said aspirating passage, said passage extending through said tubular-shaped extending portion, a hollow needle attached to said tubular-shaped extending portion, a generally cylindrical-shaped member of said handpiece extending and enclosing said tubular-shaped extending portion to form a cavity and irrigation means adapted to supply irrigation fluid to said cavity and to an operating site at an end of said needle a and an opening formed in said ultrasonic motor between said aspirating passage and said cavity so as to remove bubbles from the irrigation fluid.

2. An ultrasonic handpiece according to claim 1 wherein said opening is substantially linear and makes an angle of sixty degrees with the longitudinal axis of said handpiece.

* * * * *